United States Patent
Woo et al.

(10) Patent No.: US 7,704,526 B2
(45) Date of Patent: Apr. 27, 2010

(54) SUSTAINED RELEASE COMPOSITION FOR ORAL ADMINISTRATION OF DRUGS

(75) Inventors: Jong-Soo Woo, Suwon-si (KR); Moon-Hyuk Chi, Suwon-si (KR)

(73) Assignee: Hanmi Pharm. Co., Ltd, Kyungki-do (KR)

( * ) Notice: Subject to any disclaimer, the term of this patent is extended or adjusted under 35 U.S.C. 154(b) by 1406 days.

(21) Appl. No.: 10/650,931

(22) Filed: Aug. 27, 2003

(65) Prior Publication Data
US 2004/0081693 A1 Apr. 29, 2004

(30) Foreign Application Priority Data
Oct. 23, 2002 (KR) .................. 10-2002-0064940

(51) Int. Cl.
*A61K 31/4422* (2006.01)
*A61K 31/351* (2006.01)
*A61K 9/22* (2006.01)

(52) U.S. Cl. ................. 424/468; 514/460; 514/356

(58) Field of Classification Search ............. None
See application file for complete search history.

(56) References Cited

U.S. PATENT DOCUMENTS

| | | | |
|---|---|---|---|
| 4,765,984 A * | 8/1988 | Vellekoop et al. ........ 424/441 | |
| 4,792,452 A | 12/1988 | Howard et al. | |
| 5,846,563 A * | 12/1998 | Baichwal ................. 424/457 |
| 6,264,981 B1 * | 7/2001 | Zhang et al. ............ 424/451 |
| 6,416,786 B1 * | 7/2002 | Mulye et al. ........... 424/468 |
| 6,465,014 B1 * | 10/2002 | Moroni et al. .......... 424/486 |
| 6,656,470 B2 * | 12/2003 | Bowersock et al. ..... 424/184.1 |

FOREIGN PATENT DOCUMENTS

WO 97/39050 * 10/1997

* cited by examiner

*Primary Examiner*—Phyllis G. Spivack
(74) *Attorney, Agent, or Firm*—Sughrue Mion, PLLC (57) ABSTRACT

A sustained-release composition for oral administration of a drug, comprising the drug, a mixture of sodium alginate and xanthan gum as a carrier for sustained release and a mixture of hydroxypropyl methylcellulose and propylene glycol alginate as a gel hydration accelerator, which is capable of maintaining a constant drug level in blood for 24 hours or more. Due to rapid gel hydration without forming a non-gelated core, the drug release rate follows zero order kinetics and does not significantly vary with the degree of gastrointestinal motility.

4 Claims, 9 Drawing Sheets

SUSTAINED RELEASE COMPOSITION FOR ORAL ADMINISTRATION OF DRUGS

FIELD OF THE INVENTION

The present invention relates to a sustained-release composition for oral administration of a drug, comprising the drug, a carrier for sustained release of the drug and a gel hydration accelerator, which is capable of maintaining a constant drug level in blood for 24 hours or more.

BACKGROUND OF THE INVENTION

Once injected, the in vivo activity of a drug lasts only a short period of time and, for this reason, repeated administration of the drug is required for a long-term treatment. For example, in order to treat hypertension, drugs such as nifedipine should be administered more than 3 times a day.

Accordingly, there have been numerous efforts to develop a sustained-release formulation which can maintain an effective in vivo drug level for more than 24 hours. For instance, Japanese Patent Publication No. 6001716A (1994. Jan. 11) discloses a solid dispersion formulation based on a hydroxypropyl methylcellulose matrix, and European Patent Publication No. 521310A (1993. Jan. 7), a formulation based on a mixture of hydroxypropyl cellulose and hydroxypropyl methylcellulose which is a water-soluble polymer gelation agent. Further, Japanese Patent Publication No. 62077335A (1987. Apr. 9) teaches a gel forming formulation based on carboxyvinyl polymer; Japanese Patent Publication No. 03169814A (1991. Jul. 23), a formulation based on a mixture of a water-soluble polymer such as hydroxypropyl cellulose, hydroxypropyl methylcellulose, polyvinyl pyrrolidone and methylcellulose, and a water insoluble polymer such as microcystal cellulose; and European Patent No. 274176B (1992. May 27), a sustained release formulation based on polyvinyl pyrrolidone. However, these formulations have the drawback that a constant rate of drug release cannot be maintained for more than 24 hours due to the formation of a gel membrane on the outer shell of the formulation, leaving a non-gelated core.

Further, U.S. Pat. Nos. 4,765,989A, 5,208,037A and 5,019,397A report osmotic release control formulations that exhibit a constant rate of drug release rate following zero order kinetics. However, the manufacturing process of such formulations is very complicated and costly, besides the problem that the drug contained therein is not fully bioavailable (John S Grundy and Robert T. Foster, Clin. Pharmacokinet, 30(1): 28-51(1996)).

The present inventors have previously reported that a formulation of a drug prepared by using a monoglyceride gel carrier releases the drug at a constant rate that follows zero order kinetics for 24 hours, when brought into contact with a hydrophilic matrix or a water soluble matrix (Korean Patent No. 10-0216624 (1999. May 31)). However, this formulation is of an erosion type and has the problem of easy degradation by contractive movements of the gastrointestinals.

SUMMARY OF THE INVENTION

Accordingly, it is an object of the present invention to provide a sustained release composition for oral administration of a drug, which, upon in vivo administration, is capable of releasing the drug at a constant rate following zero order kinetics for 24 hours or more, the rate being affected little by the degree of gastrointestinal motility.

In accordance with one aspect of the present invention, there is provided a sustained-release composition for oral administration of a drug, comprising the drug, a carrier for sustained release of the drug and a gel hydration accelerator.

BRIEF DESCRIPTION OF DRAWINGS

The above and other objects and features of the present invention will become apparent from the following description of the invention taken in conjunction with the following accompanying drawings, which are respectively show.

DETAILED DESCRIPTION OF THE INVENTION

The sustained-release composition for oral administration of the present invention comprises a drug, comprising the drug, a carrier for sustained release of the drug and a gel hydration accelerator.

The carrier is preferably a mixture of sodium alginate and xanthan gum, and the gel hydration accelerator, a mixture of hydroxypropyl methylcellulose and propylene glycol alginate.

The sustained-release composition of the present invention can maintain a constant drug level in the blood for 24 hours or more owing to the fact that the drug release rate follows zero order kinetics and does not significantly vary with the degree of gastrointestinal motility due to rapid gel hydration without forming a non-gelated core.

The components of the inventive composition are described in detail as follows:

(1) Pharmacologically Active Ingredient (Drug)

The pharmacologically active ingredient of the inventive composition is any one of those drugs which are suitable for use in sustained-release drug formulations. Exemplary drugs include antihypertensive drugs such as nifidipine, doxazocin, amosulralol, felodipine, lercanidipine, lacidipine, nicardipine, fosinopril, imidapril, clizapril, perindopril, lisinopril, losartan, irvesartan and candesartan; drugs for cardiovascular diseases such as isradipine; drugs for hyperlipemia such as lovastatin and simvastatin; non-steroidal anti-inflammatory drugs; drugs for asthma; anti-diabete drugs such as gliclazide, glimepiride and glipizide; calmative; antibiotic; antispasmodic; antispasmodic; and steroids, preferably nifedipine.

(2) Carrier for Sustained Release

The carrier for sustained release of the inventive composition is preferably a mixture of sodium alginate and xanthan gum with a mix ratio (weight by weight) in the range of 1:0.1~10, preferably, 1:0.2~0.6 to reduce initial burst release and change in the released amount of the drug.

Further, in order to enhance the structural integrity of the formulation, the inventive carrier may further comprise locust bean gum, the weight ratio of sodium alginate:xanthan gum: locust bean gum being the range of 1:0.2~10:0.1~5, preferably, 1:1~5:0.5~3.

(3) Gel Hydration Accelerator

The gel hydration accelerator used in the present invention plays a critical role in forming a homogenous gelated core without leaving a non-gelated portion when the formulation is brought into contact with an aqueous medium. The gel hydration accelerator of the inventive composition is preferably a mixture of hydroxypropyl methylcellulose and propylene glycol alginate with a mix ratio (weight by weight) in the range of 1:0.05~20, preferably, 1:0.1~10. The hydroxypropyl methylcellulose used therein preferably has a viscosity ranging from 4,000 to 100,000 cps.

In accordance with the composition of the present invention, the weight ratio of the drug:the carrier for sustained release:the gel hydration accelerator is in the range of 1:3~30: 0.1~15, preferably, 1:5~25:0.5~10.

The pharmaceutical composition of the present invention may be formulated for oral administration. The composition for oral administration may take various forms such as tablet, pill, powder, sachet, elixir, suspension, emulsion, solution, syrup, aerosol, granule, soft and hard gelatin capsule and the like, which may contain conventional additives such as a diluent (e.g., lactose, dextrose, sucrose, mannitol, sorbitol, cellulose and/or glycine), a lubricant (e.g., silica, talc, stearic acid or its zinc, magnesium or calcium salt and/or polyethylene glycol). In the tablet form, the composition may further comprise a binder (e.g., magnesium aluminum silicate, starch paste, gelatin, tragacanth, methyl cellulose, sodium carboxymethyl cellulose and/or polyvinylpyrrolidine, hydroxyprophyl cellulose and/or kopovidone (Kollidon VA64®, BASF, Germany) and optionally a disintegrant (e.g., starch, agar and alginic acid or its sodium salt), fizzy water and/or absorbent, colorant, flavor and sweetener.

The compositions may additionally include fillers, preservatives, anti-oxidants, stabilizers, pigments, anti-agglutinating agents, lubricating agents, wetting agents, flavoring agents, emulsifiers and the like.

The inventive pharmaceutical composition may be administered daily. A typical daily dose of the active ingredient ranges from about 0.15 to 2 mg/kg, preferably 0.5 to 1.5 mg/kg, and can be administered in a single dose or in divided doses. However, it should be understood that the amount of the active ingredient actually administered should be determined in light of various relevant factors including the condition to be treated, the chosen route of administration, the age and weight of the individual patient, and the severity of the patient's symptoms; and, therefore, the dosage suggested above should not be construed to limit the scope of the invention in any way.

The following Examples and Test Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLES 1 TO 21

Preparation of Tablet

Nifedipine(Unique Chemicals, India), isradipine(Sun Pharm. India), lovastatin(CKD Pharm. KOREA), glipizide (Sun Pharm. India), sodium alginate(Keltone® HVCR, Keltoen® LVF, Kelcosol®, Kelset®, ISP USA), xanthan gum (Keltrol® F, Kelco, USA), Locust bean Gum(Cesagum® LN1,LR 200, Cesalpinia, Italy), propylene glycol alginate (Kelcoloid HVF, LVF, ISP, USA), hydroxypropyl methylcellulose (Meltose 90SH, 4,000SR, 100,000SR, Shin-Etsu, Japan) and kofovidone (Kollidon VA64, BASF, Germany) were mixed as shown in Table 1 for 30 minutes, magnesium stearate and light anhydrous silicic acid (finer than mesh 30) were added thereto, and mixed for 5 minutes. Then, the resulting mixture was tableted under the common presser in accordance with the tablet preparation method to obtain a tablet preparation.

TABLE 1

| | The drug | | | | | Hydroxypropyl methylcellulose | | | | |
| | The kinds | The amount | Sodium alginate | Xanthan gum | Locust bean gum | Propyleneglycol alginate | The viscosity (cps) | The amount | Kopovidone | Light anhydrous silicic acid | Magnesium stearate |
|---|---|---|---|---|---|---|---|---|---|---|---|
| 1 | Nifedipine | 33 | 500 | 125 | — | 10 | 100,000 | 45 | 25 | 7 | 2 |
| 2 | Nifedipine | 33 | 400 | 100 | — | 20 | 4,000 | 40 | 10 | 7 | 2 |
| 3 | isradipine | 10 | 300 | 100 | — | 5 | 100,000 | 30 | 20 | 5 | 2 |
| 4 | lovastatin | 60 | 550 | 140 | — | 5 | 100,000 | 40 | 30 | 7 | 2 |
| 5 | glipizide | 10 | 400 | 50 | — | 5 | 100,000 | 40 | 25 | 7 | 2 |
| 6 | Nifedipine | 33 | 300 | 50 | — | 10 | 100,000 | 45 | 25 | 7 | 2 |
| 7 | Nifedipine | 33 | 325 | 50 | — | 10 | 100,000 | 45 | 25 | 7 | 2 |
| 8 | Nifedipine | 33 | 350 | 50 | — | 10 | 100,000 | 45 | 25 | 7 | 2 |
| 9 | Nifedipine | 33 | 375 | 50 | — | 10 | 100,000 | 45 | 25 | 7 | 2 |
| 10 | Nifedipine | 33 | 400 | 50 | — | 10 | 100,000 | 45 | 25 | 7 | 2 |
| 11 | Nifedipine | 33 | 450 | 50 | — | 10 | 100,000 | 45 | 25 | 7 | 2 |

TABLE 1-continued

| The kinds | The drug | | Locust bean gum | Propyleneglycol alginate | Hydroxypropyl methylcellulose | | Kopovidone | Light anhydrous silicic acid | Magnesium stearate |
|---|---|---|---|---|---|---|---|---|---|
| | The amount | Sodium alginate | Xanthan gum | | The viscosity (cps) | The amount | | | |

COMPARATIVE EXAMPLES 1 TO 4

Preparation of Tablet

Comparative tablets were prepared by the procedure of Example 1 except that the ingredients listed in Table 2 were employed:

TABLE 2

| | The drug | | | Locust bean gum | Propyleneglycol alginate | Hydroxypropyl methylcellulose | | Kopovidone | Light anhydrous silicic acid | Magnesium stearate |
|---|---|---|---|---|---|---|---|---|---|---|
| | The kinds | The amount | Sodium alginate | Xanthan gum | | | The viscosity (cps) | The amount | | | |
| 1 | Nifedipine | 33 | 60 | 180 | 60 | — | 100,000 | — | 25 | 10 | 2 |
| 2 | Nifedipine | 10 | 10 | 200 | 90 | 100 | 100,000 | 100 | 25 | 10 | 2 |
| 3 | Nifedipine | 33 | 30 | 450 | — | 125 | 100,000 | 25 | 25 | 10 | 2 |
| 4 | Nifedipine | 33 | 60 | 180 | 60 | 150 | 100,000 | 5 | 25 | 10 | 2 |

TEST EXAMPLE 1

In Vitro Release-Test

Figure 1A:
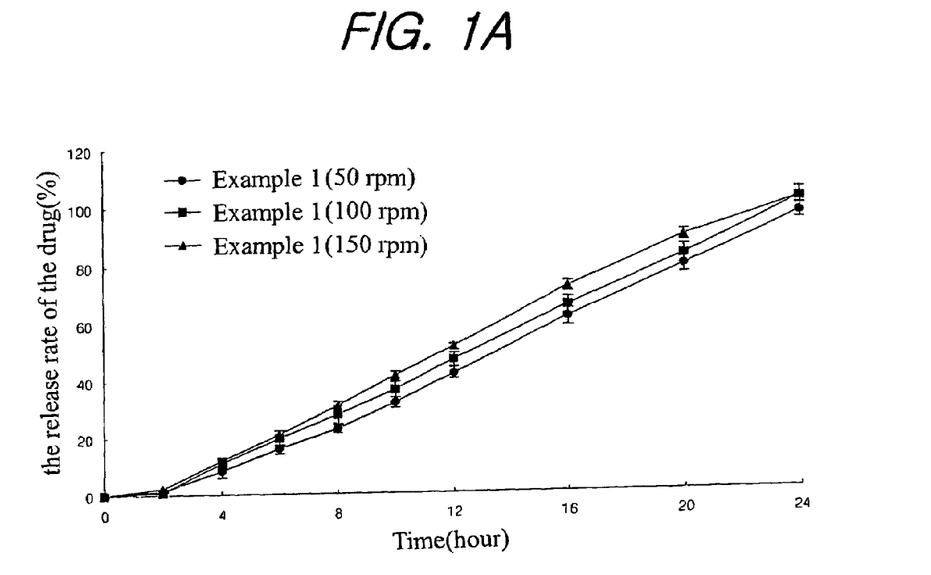
FIGS. 1A and 1B: the time-dependent changes in the amount of the drug released in vitro (A: the formulation of the present invention; and B: the formulation of Korean Patent No. 10-0216624)
Figure 1B:
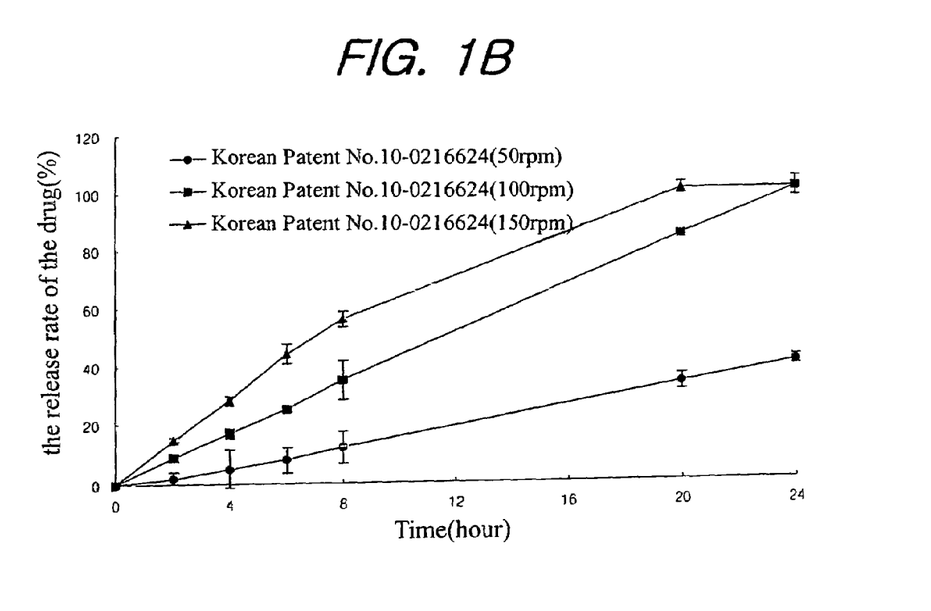

The tablet prepared in Example 1 and the formulation described according to Korean Patent No. 10-0216624 were subjected to in vitro release-test in accordance with the release-test method described in Korea pharmacopoeia (the paddle method). The amount of released nifedipine from each of the tablets during the in vitro release-test conducted under the following conditions was measured by liquid chromatography. In order to avoid the drug degradation, the above tests were carried out at a long wavelength ($\lambda > 420$ nm)
  release-test system: Erweka DT 80
  release solution: the first release-test using 500 ml of artificial gastric juice (pH 1.2) for 2 hours and the secondary release-test using 400 ml of 0.235 M $Na_2HPO_4$ containing 2.25% sodium lauryl sulfate(SLS) for 22 hours (a total release solution: pH 6.8, 1% SLS)
  temperature of release solution: 37±0.5° C.
  rotation rate: 50, 100 and 150 rpm
  column: μ-Bondapak $C_{18}$® (Waters)
  mobile phase: acetonitrile:water (55:45 v/v)
  flow rate: 1.2 ml/min.
  detector: ultraviolet spectrophotometer (350 nm)
  injection volume: 20 μl
  calculation of released amount: cumulative release amount The time-dependent changes in the amount of nifedipine released are shown in FIG. 1(A: the formulation of the present invention and B: the formulation of Korea Patent No. 10-0216624). As shown in FIG. 1, the time-dependent changes in the in vitro release pattern of the inventive formulation differ from that of the formulation of Korea Patent No. 10-0216624, exhibiting a steady release pattern which does not vary significantly with the degree of gastrointestinal motility.

TEST EXAMPLE 2

In Vitro Release-Test

Figure 2:
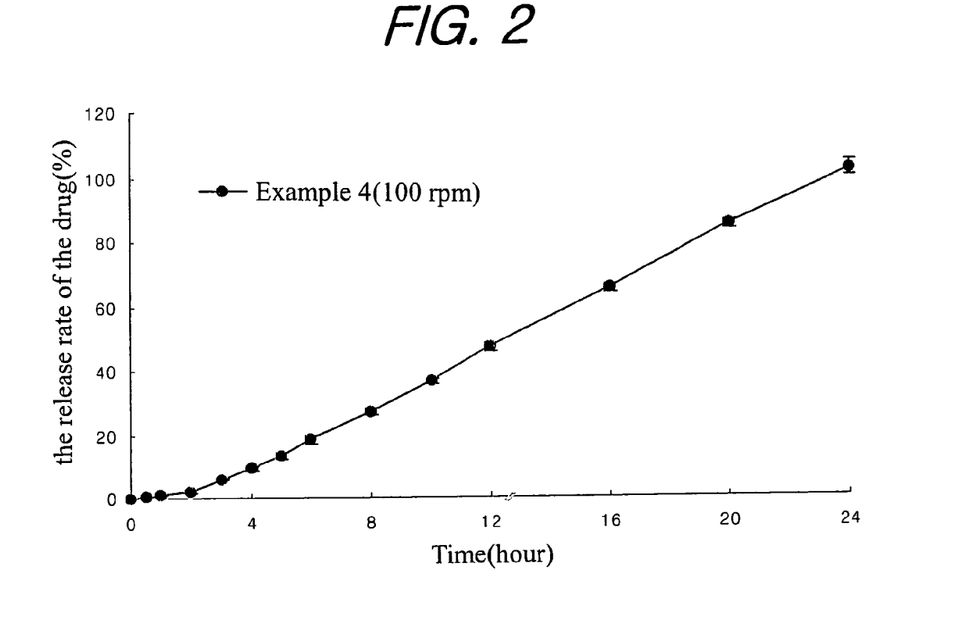
FIG. 2: the time-dependent changes in the amount of the drug released in vitro by the formulation of the present invention.

An in vitro release-test was conducted by employing the formulation prepared in Example 1 in accordance with the method of Test Example 1. The result in FIG. 2 shows that the lovastatin formulation releases the drug at a constant release rate following zero order kinetics for 24 hours.

TEST EXAMPLE 3

In Vitro Release-Test

Figure 3A:
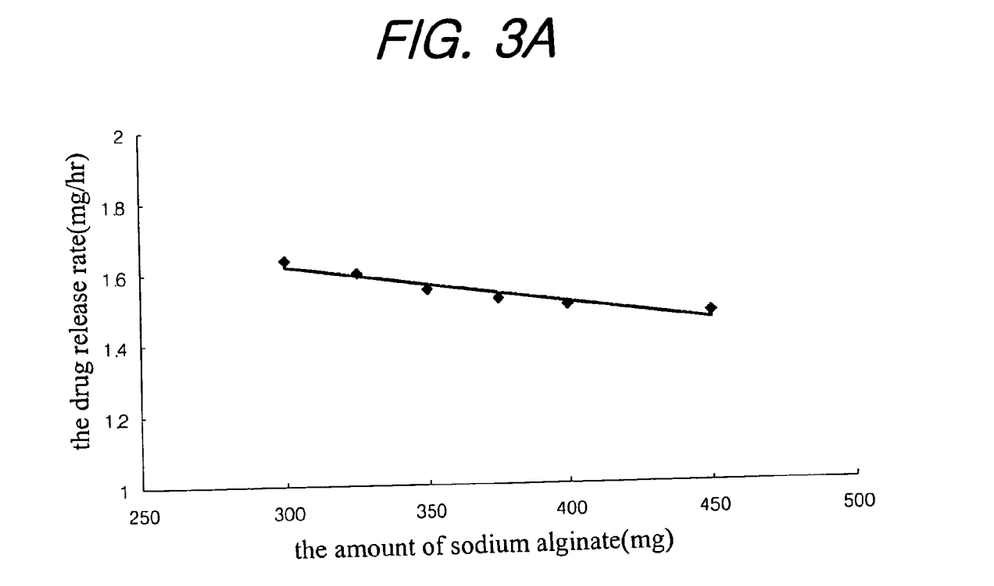
FIGS. 3A and 3B: dependencies of the drug release rate and the drug release lag time on the amount of sodium alginate.
Figure 3B:
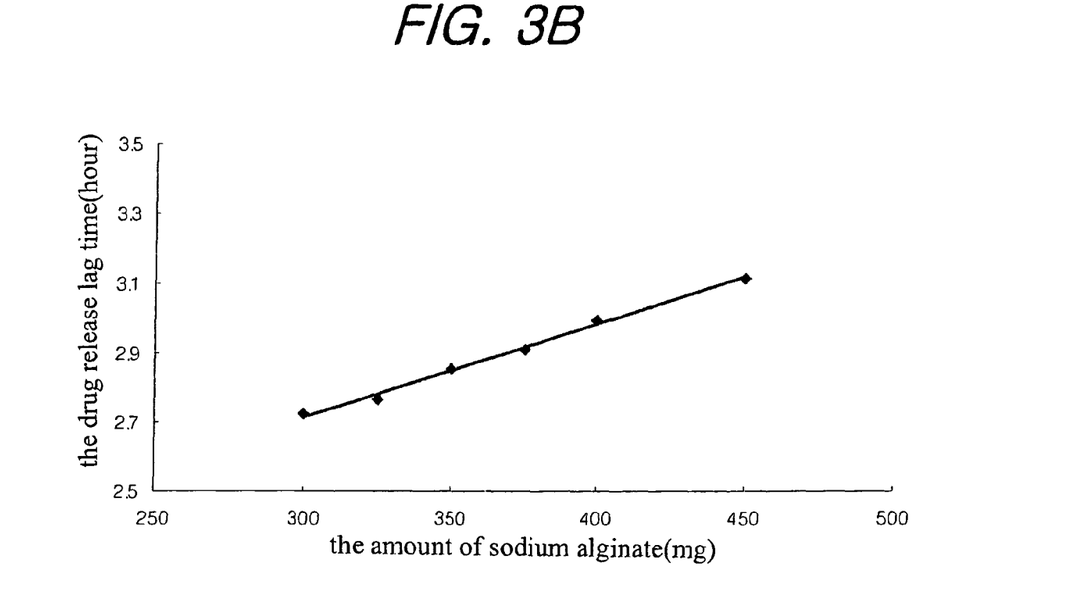

In order to examine whether the release rate of the drug depends on the amount of sodium alginate of the carrier, an in vitro release-test was conducted by employing the formulations prepared in Examples 6 to 11 in accordance with the method of Test Example 1. The result in FIG. 3(A: the release rate of the drug and B: the release lag time of the drug) shows that the release rate of the drug becomes proportionally slower and the release lag time of the drug, longer, with the amount of sodium alginate.

TEST EXAMPLE 4

In Vitro Release-Test

Figure 4A:
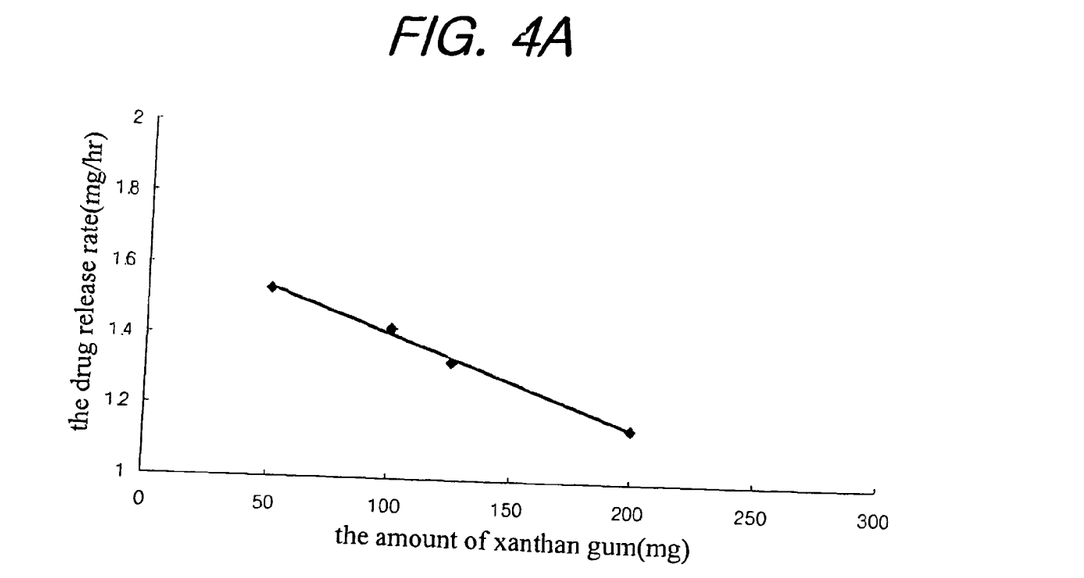
FIGS. 4A and 4B: dependencies of the drug release rate and the drug release lag time on the amount of xanthan gum.
Figure 4B:
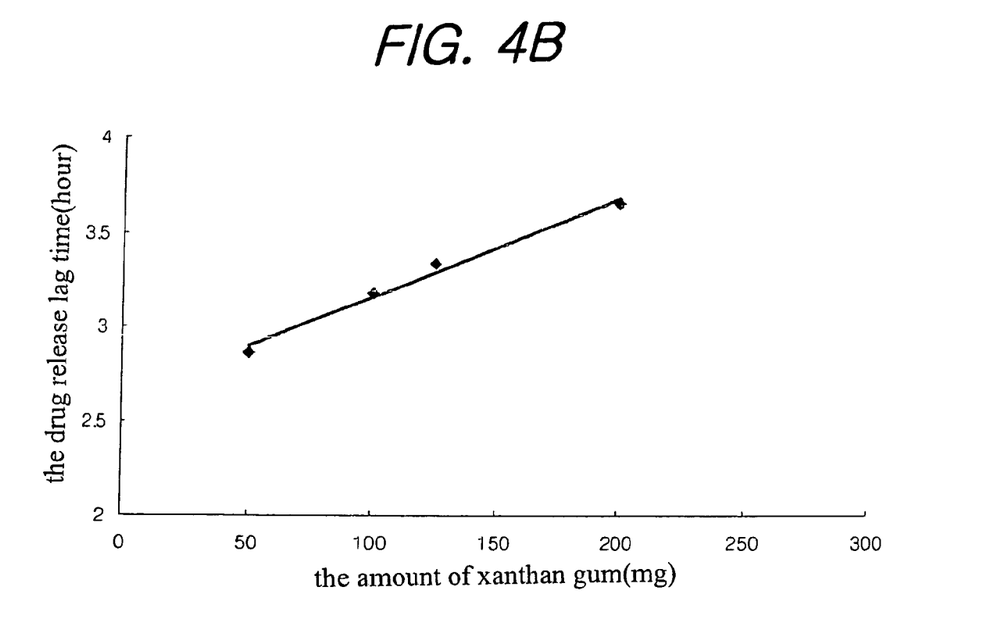

Also, in order to examine whether the release rate of the drug depends on the amount of xanthan gum of the carrier, an in vitro release-test was conducted by employing the formulations prepared in Examples 12 to 14 in accordance with the method of Test Example 1. The result in FIG. 4 (A: the release rate of the drug and B: the release lag time of the drug) shows that the release rate of the drug becomes proportionally slower, and the release lag time of the drug, longer, with the amount of xanthan gum.

TEST EXAMPLE 5

In Vitro Release-Test

Figure 5A:
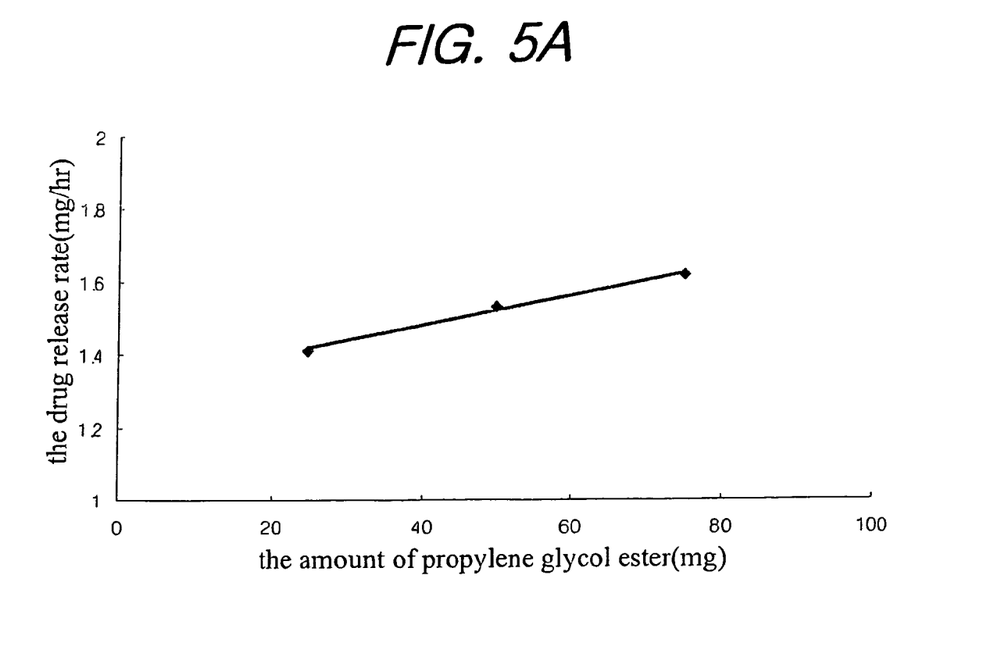
FIGS. 5A and 5B: dependencies of the drug release rate and the drug release lag time on the amount of propylene glycol ester.
Figure 5B:
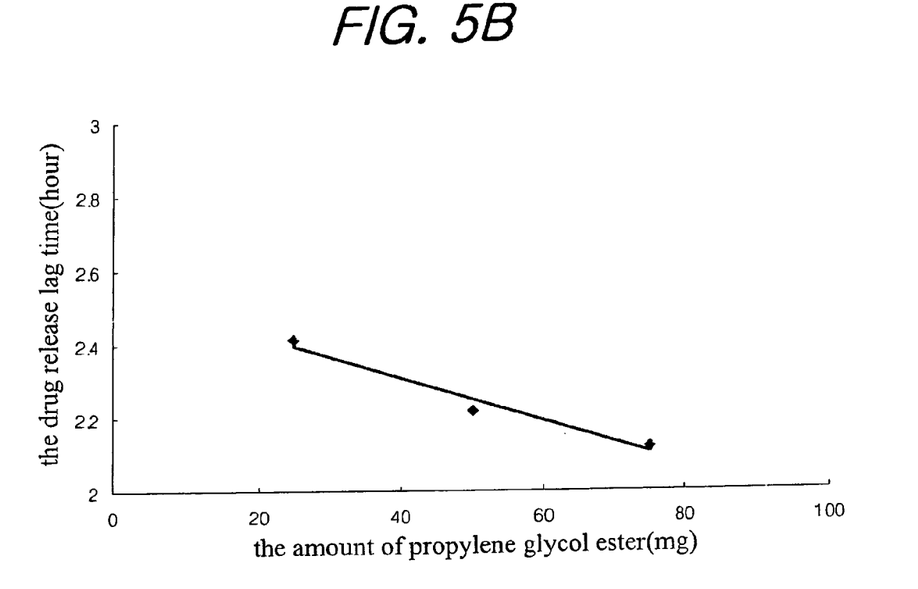

In order to examine whether the release rate of the drug depends on the amount of propyleneglycol alginate of the gel hydration accelerator, an in vitro release-test was conducted by employing the formulations prepared in Examples 15 to 17 in accordance with the method of Test Example 1. The result in FIG. 5 (A: the release rate of the drug and B: the release lag time of the drug) shows that the release rate of the drug becomes proportionally higher, and the release lag time of the drug, shorter, with the amount of propyleneglycol alginate.

TEST EXAMPLE 6

In Vitro Release-Test

Figure 6A:
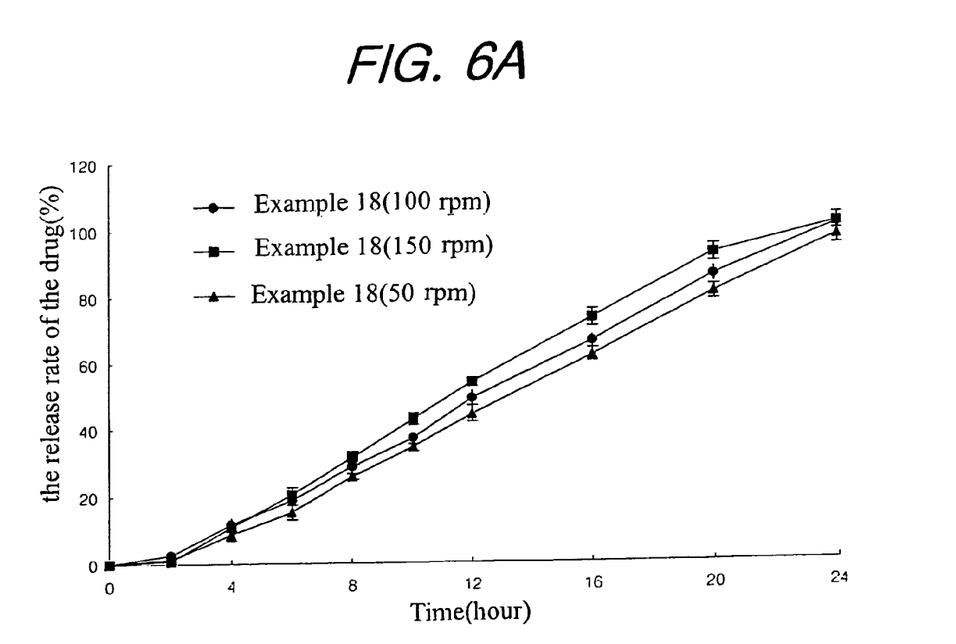
FIGS. 6A and 6B: the drug release rate changes with the amount of the carrier for sustained release (A: the formulation prepared in Example 18; and B: the formulation prepared in Example 19)
Figure 6B:
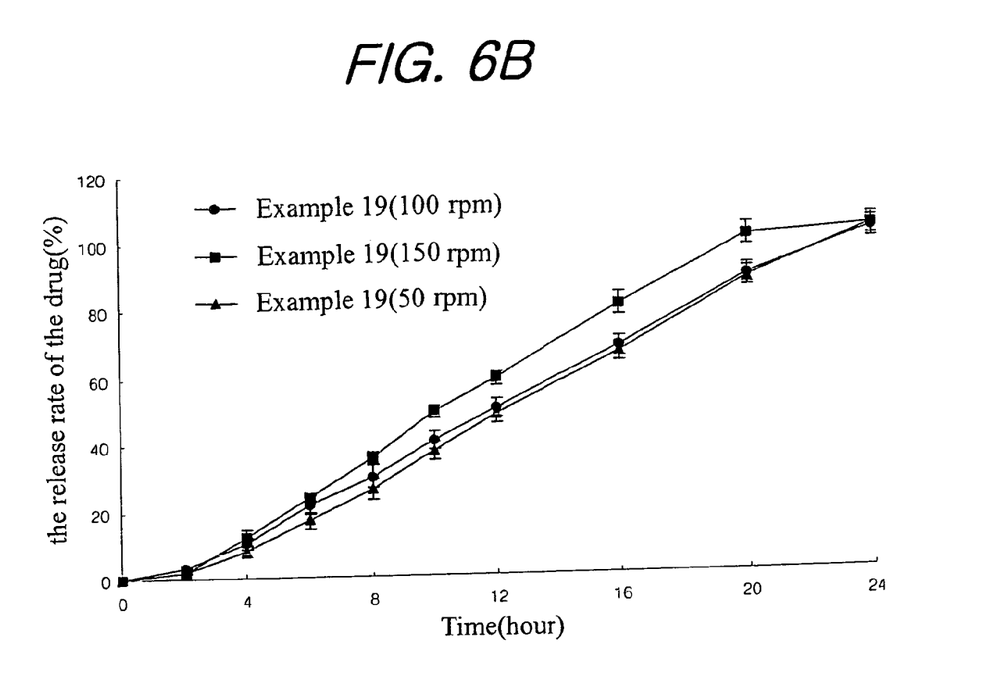

In order to examine whether the release rate of the drug depends on the amount of the carrier, an in vitro release-test was conducted by employing the formulations prepared in Examples 18 and 19 in accordance with the method of Test Example 1. The result in FIGS. 6A and 6B (A: the formulation of Example 18 and B: the formulation of Example 19) shows that the release rate of the drug follows zero order kinetics which does not depend on the amount of the carrier. That is, the formulations release the drug more or less at a constant rate when the mix ratio of the compounds of the carrier is unchanged.

TEST EXAMPLE 7

In Vitro Release-Test

Figure 7A:
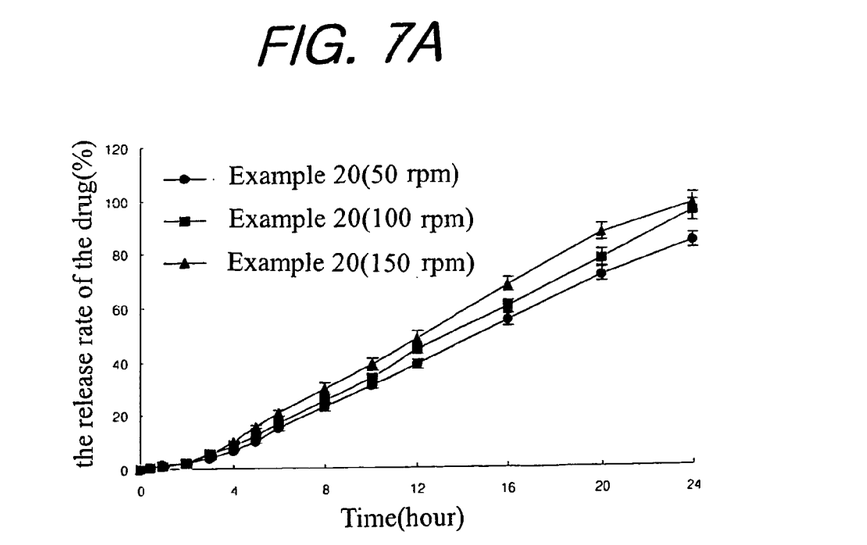
FIGS. 7A and 7B: the drug release rate changes observed when locust bean gum is added to the carrier (A: the formulation prepared in Example 20; and B: the formulation prepared in Example 21)
Figure 7B:
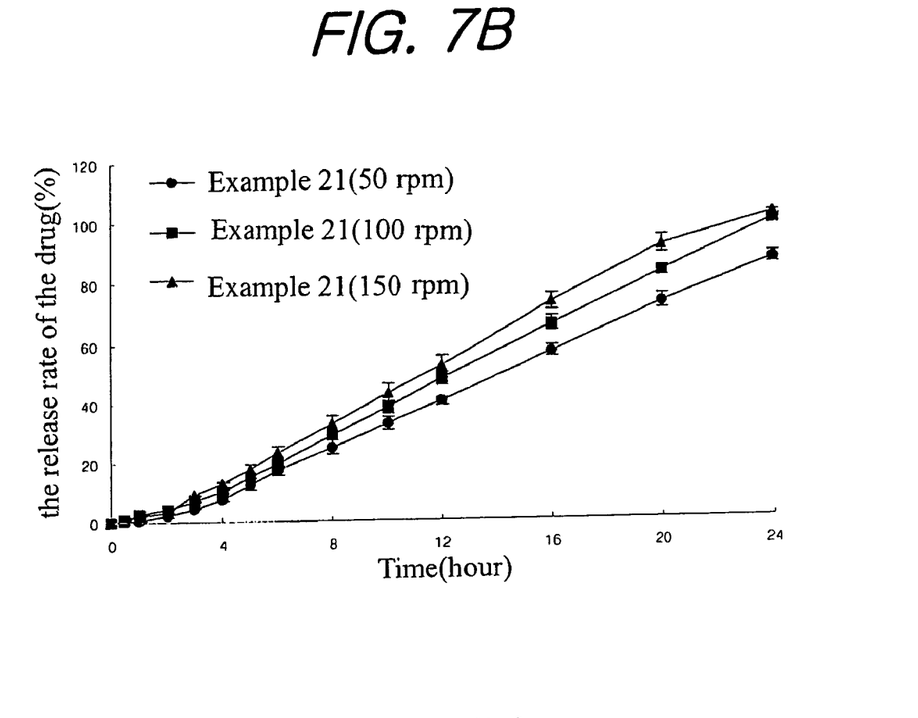
Figure 8A:
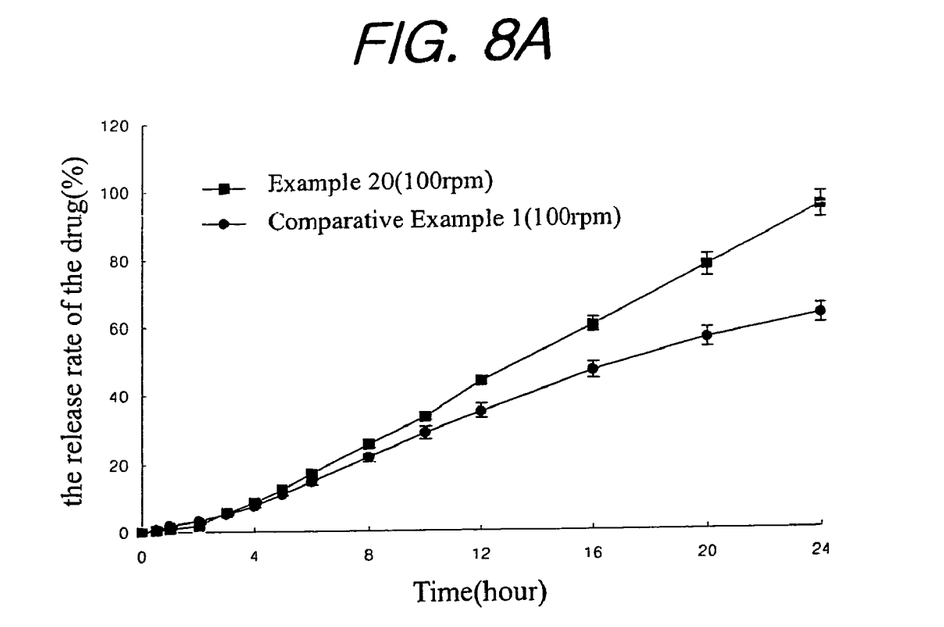
FIGS. 8A to 8D: the time-dependent changes in the amount of the drug released in vitro by the inventive sustained-release formulation as compared with those of comparative formulations (A: Comparative Example 1; B: Comparative Example 2; C: Comparative Example 3; and D: Comparative Example 4).
Figure 8B:
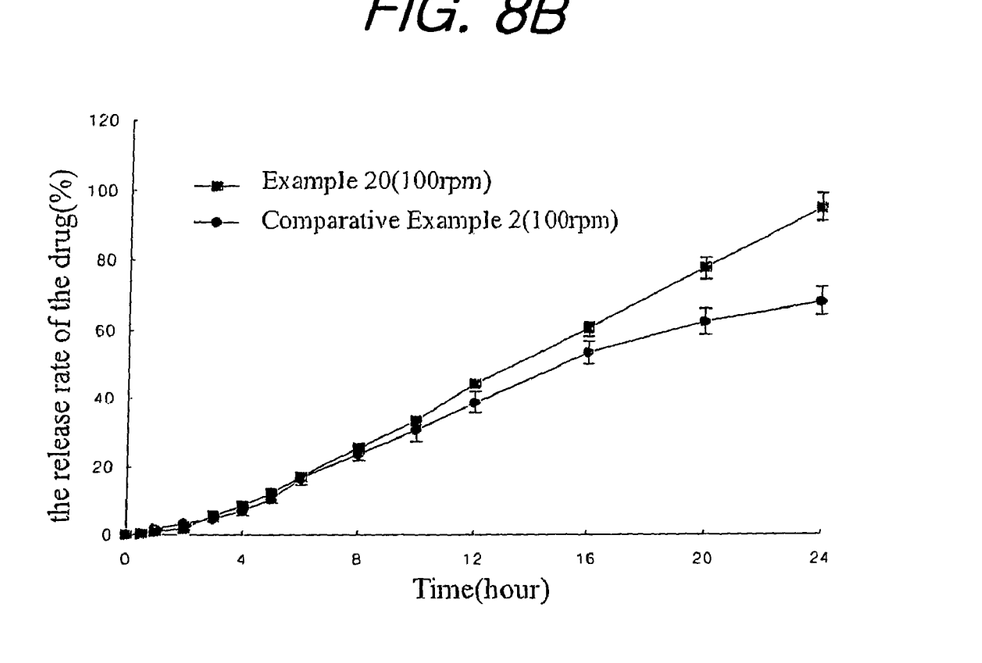
Figure 8C:
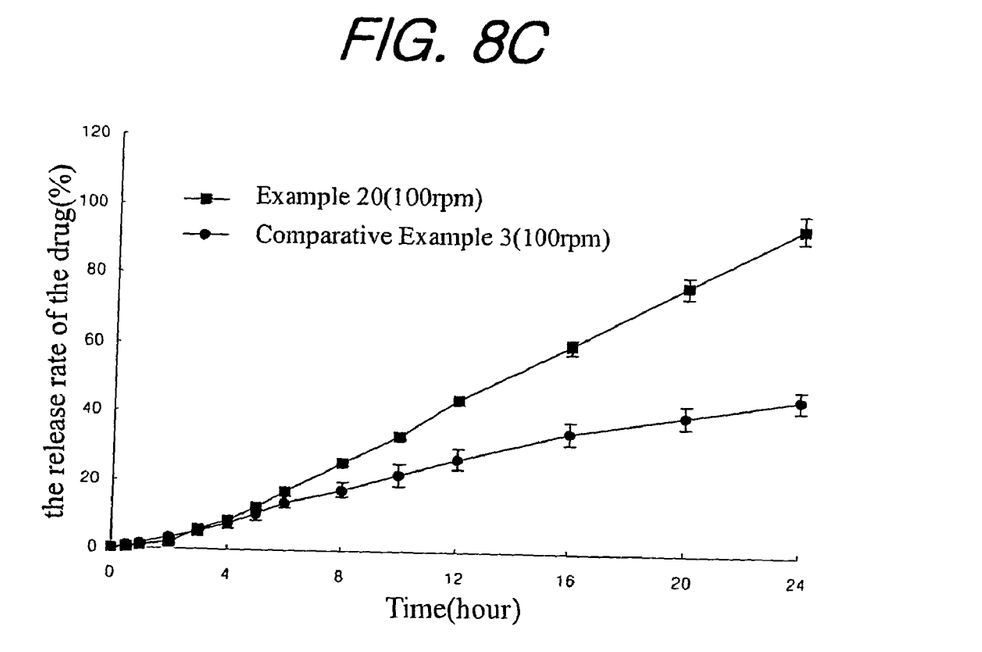
Figure 8D:
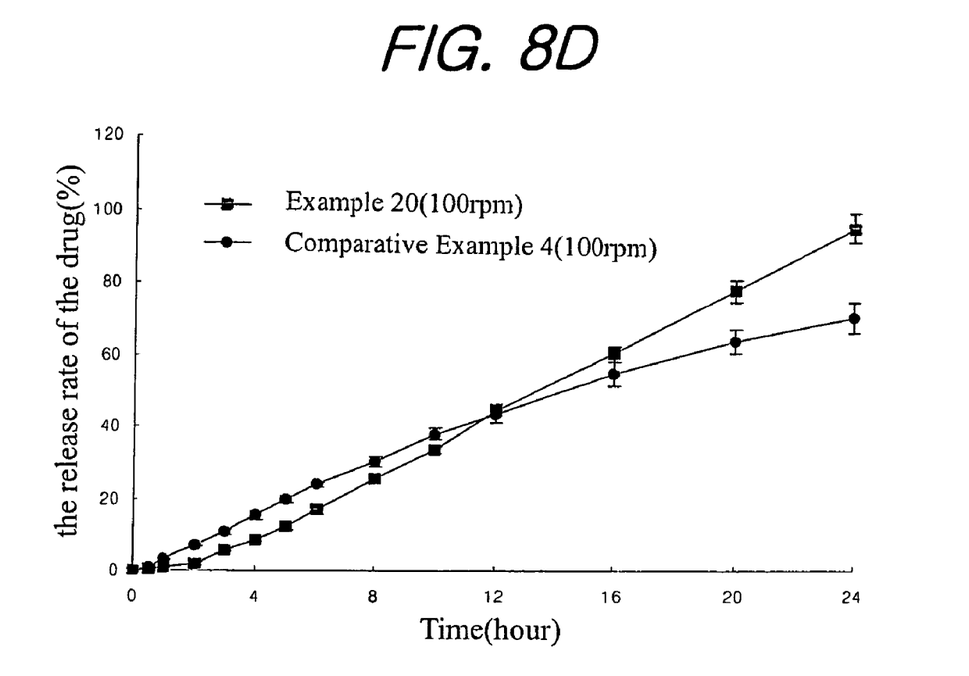

In order to examine whether the release rate of the drug changes when locust bean gum is added to the carrier, an in vitro release-test was conducted by employing the formulations prepared in Examples 20 and 21 in accordance with the method of Test Example 1. The result in FIGS. 7A and 7B (A: the formulation of Example 20 and B: the formulation of Example 21) shows that the formulation using a mixture of sodium alginate, xanthan gum and locust bean gum as the carrier has an excellent sustained release.

TEST EXAMPLE 8

In Vitro Release-Test and Measurement of the Formation Rate of Non-Gelated Core and Gelated Core In order to compare the release rates of the inventive and other formulations, an in vitro release-test was conducted by employing the formulations prepared in Example 20 and Comparative Examples 1 to 4 in accordance with the method of Test Example 1. The result in FIGS. 8A to 8D (A: Comparative Example 1; B: Comparative Example 2; C: Comparative Example 3; and D: Comparative Example 4) shows that the time-dependent changes in the in vitro release pattern of the formulations prepared in Comparative Examples 1 to 4 differ from that of the inventive formulation. That is, the comparative formulations failed to exhibit zero order kinetics.

Further, at day 4 of the test, sections of the tablets were examined to determine the extents of gelated core and non-gelated core in accordance with the method of K. N. Park et al. (*Controlled Drug Delivery*, 18-23(2000)). The results are shown in Table 3.

TABLE 3

|  | Non-gelated core | Gelated core | Gelated core/ Non-gelated core |
|---|---|---|---|
| Example 20 | 0.09 ± 0.04 cm | 0.73 ± 0.03 cm | 8.11 ± 0.45 |
| Comparative Example 1 | 0.39 ± 0.03 cm | 0.36 ± 0.04 cm | 0.92 ± 0.13 |
| Comparative Example 2 | 0.30 ± 0.03 cm | 0.54 ± 0.02 cm | 1.85 ± 0.14 |
| Comparative Example 3 | 0.32 ± 0.02 cm | 0.46 ± 0.03 cm | 1.44 ± 0.05 |
| Comparative Example 4 | 0.20 ± 0.01 cm | 0.54 ± 0.03 cm | 2.72 ± 0.14 |

As shown in Table 3, the extent of core gelation is much more extensive for the inventive formulation than the formulations prepared in Comparative Examples 1 to 4.

While the invention has been described with respect to the above specific embodiments, it should be recognized that various modifications and changes may be made and also fall within the scope of the invention as defined by the claims that follow.

What is claimed is:

1. A sustained-release composition for oral administration of a drug selected from the group consisting of nifedipine and lovastatin, comprising the drug, a carrier for sustained release of the drug and a gel hydration accelerator, said composition being delivered to the gastrointestinal tract where the drug is released at a constant rate following zero order kinetics over a period of 24 hours or more, wherein the weight ratio of the drug: the carrier for sustained release of the drug: the gel hydration accelerator is in the range of 1:3 to 30:0.1 to 15; the carrier is a mixture of sodium alginate and xanthan gum having a weight ratio of 1:1 to 10; and the gel hydration accelerator is a mixture of hydroxypropyl methylcellulose and propylene glycol alginate having a weight ratio of 1:0.05 to 20.

2. The composition of claim 1, wherein the carrier further comprises locust bean gum.

3. The composition of claim 2, wherein the weight ratio of sodium alginate : xanthan gum: locust bean gum is in the range of 1:0.2 to 10: 0.1 to 5.

4. A sustained-release composition for oral administration of a drug selected from the group consisting of nifedipine and lovastatin, comprising the drug, a mixture of sodium alginate and xanthan gum, and a mixture of hydroxypropyl methylcellulose and propylene glycol alginate, wherein the weight ratio of the drug: the mixture of sodium alginate and xanthan gum : the mixture of hydroxypropyl methylcellulose and propylene glycol alginate is in the range of 1:3 to 30:0.1 to 15; sodium alginate and xanthan gum have a weight ratio of 1:0.1 to 10; and hydroxypropyl methylcellulose and propylene glycol alginate have a weight ratio of 1:0.05 to 20.

* * * * *